United States Patent [19]

Golding et al.

[11] Patent Number: 5,049,134
[45] Date of Patent: Sep. 17, 1991

[54] SEALLESS HEART PUMP

[75] Inventors: Leonard A. R. Golding, Moreland Hills; William A. Smith, Lyndhurst; Warren F. Wade, Orange Village, all of Ohio

[73] Assignee: The Cleveland Clinic Foundation, Cleveland, Ohio

[21] Appl. No.: 349,000

[22] Filed: May 8, 1989

[51] Int. Cl.⁵ .......................... A61M 1/00; A61N 5/00
[52] U.S. Cl. ........................................ 604/151; 623/3; 415/900; 417/423.1
[58] Field of Search ............... 604/151, 4, 49; 600/16; 623/3; 128/DIG. 3; 417/420, 423.1, 423.12–423.14, 424.1, 424.2, 366, 371, 372, 352–354, 368; 415/110, 111, 176, 900

[56] References Cited

U.S. PATENT DOCUMENTS

| | | | |
|---|---|---|---|
| 3,420,184 | 1/1969 | Englesberg et al. | 623/3 |
| 3,608,088 | 9/1971 | Dorman et al. | 633/3 |
| 3,647,324 | 3/1972 | Rafferty et al. | 623/3 |
| 3,960,468 | 6/1976 | Boorse et al. | 417/423.13 |
| 4,135,253 | 1/1979 | Reich et al. | 415/900 |
| 4,382,199 | 5/1983 | Isaacson | 623/3 |
| 4,625,712 | 12/1986 | Wampler | 415/900 |
| 4,645,733 | 2/1987 | Hauenstein | 417/420 |
| 4,688,998 | 8/1987 | Olsen et al. | 415/900 |
| 4,704,121 | 11/1987 | Moise | 623/3 |
| 4,714,405 | 12/1987 | Schaefer et al. | 417/366 |
| 4,806,080 | 2/1989 | Mizobuchi et al. | 417/353 |
| 4,812,108 | 3/1989 | Kotera | 417/423.13 |

Primary Examiner—C. Fred Rosenbaum
Assistant Examiner—Anthony M. Gutowski
Attorney, Agent, or Firm—Fay, Sharpe, Beall Fagan, Minnich & McKee

[57] ABSTRACT

A sealless centrifugal blood pump is provided in which a rotatable impeller is supported in a pump housing by fluid bearings during operation. Rotational movement of the impeller is accomplished with an inverted motor for magnetic driving of the impeller and maintenance of the axial running position of the impeller relative to the housing.

3 Claims, 3 Drawing Sheets

SEALLESS HEART PUMP

BACKGROUND OF THE INVENTION

This invention pertains to the art of pumps and more particularly to electrically driven pumps capable for use as heart pumps.

The invention is applicable to a pump device for the pumping of blood of a living person, or of a living animal, to replace or assist the pumping function of a heart. The pump is intended for intrathoracic disposition and is further capable of being sized for a fit inside the pumping chamber of a human heart. However, it will be appreciated by those skilled in the art that the invention could be readily adapted for use in other environments as, for example, where a particularly durable pump is desired which is compact in size, which does not use a shaft seal, and which avoids injury or destruction of the pumped material.

Conventional continuous flow heart assist devices have suffered from a predominant problem, the lack of relative durability due to the use of a shaft seal. Because of their intended implantation in a living being, a long life span for the pump device is a primary design objective. However, the working environment for the pump, i.e., the pumping of blood, imposes severe design conditions which have not previously been satisfactorily overcome. Most commercially available blood pumps employ a motor encased in a housing where the motor is operating in an air or saline environment. The shaft of the motor will typically extend through a sealed wall of the housing into a blood chamber to drive an impeller to urge the blood through the pump. The most common cause of failure of such prior known pumps is the failure or leakage of the seal about the shaft which either causes blood leaking into the drive compartment, or worse, saline or air leaking into the blood stream. In addition, the high shear and frictional heating occurring at the shaft-to-seal interface is prone to injure the blood and/or cause clotting.

Another problem that has occurred with prior heart pumps is stagnant blood in areas of the pump which lack sufficient wash flow. Stagnant blood will also have a tendency to clot.

Various forms of blood pumps have heretofore been suggested to overcome the problems of blood pump shaft seals. It has been found that the defects present in these prior pump devices are such that the devices are of limited economic and practical value.

In particular, it has been suggested to suspend the impeller magnetically in three dimensions to avoid the penetrating shaft into the blood chamber. However, the problems of maintaining an appropriate magnetic suspension of a rotating impeller have shown that a commercially feasible blood pump with this design is technically impractical at the present time.

Alternatively, some prior magnetically driven impellers that lack the shaft seal have not been able to overcome problems of damage to the pumped blood due to stagnant blood in some areas or have caused problems with damage to the blood at bearings which support the impeller.

The present invention contemplates a new and improved device which overcomes all of the above referred to problems and others to provide a new blood pump or pump assist device which is simple in design having only a single moving part, economical to manufacture, readily adaptable to a plurality of dimensional characteristics, sealless between the impeller and the motor, and which provides improved blood pumping.

A BRIEF SUMMARY OF THE INVENTION

In accordance with the present invention, there is provided a new centrifugal blood pump which offers a substantial improvement in pump operation and durability. The pump is capable of being implanted into a human body to assist or replace the pumping functions of the heart. The pump comprises a housing equipped with an inlet and an outlet duct. The housing includes a portion extending internally axially from an end wall toward the inlet which defines an annular chamber communicating with the inlet and outlet. An impeller is received in the chamber for selective rotation relative to the housing. The impeller also defines an internal continuous passage within the housing portion. The passage narrows at opposed ends of the impeller to define first and second fluid bearings during pump operation. A motor rotates the impeller relative to the housing.

In accordance with another aspect of the invention, the motor is inverted or "inside out" and preferably comprises a stator received in the housing and a rotor received in the impeller. The axial running position of the impeller is maintained by the magnetic forces generated between the stator and the rotor.

According to another aspect of the invention, the first and second fluid bearings include helical grooves to increase the blood flow along the bearing passageway.

In accordance with still another aspect of the present invention, the impeller includes first and second sets of blades. The first blade set is substantially larger than the second blade set and defines a main pump stage for primarily urging the blood from the inlet to the outlet. The second blade set acts as a secondary or scavenge pump to control and assist fluid flow through the first and second fluid bearings.

In accordance with another yet more limited aspect of the present invention, the impeller includes openings or "windows" connecting the main flow path to the bearing passage for further controlling fluid flow through the first and second fluid bearings. The openings may be disposed downstream of the first set of blades on the impeller.

One benefit obtained from the present invention is an implantable sealless blood pump having a single moving part that provides improved durability.

Another benefit is a provision of a blood pump which minimizes damage to the blood with improved washing about the impeller to avoid areas of likely blood stagnation or clotting.

A further benefit of the present invention is a sealless continuous flow blood pump which avoids the previous problems associated with seal to motor shaft interfaces.

Other benefits and advantages for the subject invention will become apparent to those skilled in the art upon a reading and understanding of the specification.

BRIEF DESCRIPTION OF THE DRAWINGS

The invention may take physical form in certain parts and arrangements of parts, the preferred embodiments of which will be described in detail in the specification and illustrated in the accompanying drawings which form a part hereof and wherein:

FIG. 6 is a schematic illustration of the electromagnetic reaction between a stator and operating rotor in the present invention and is intended to demonstrate the preservation of the desired axial running position of the impeller relative to the housing.

DETAILED DESCRIPTION OF THE PREFERRED EMBODIMENTS

Figure 1:
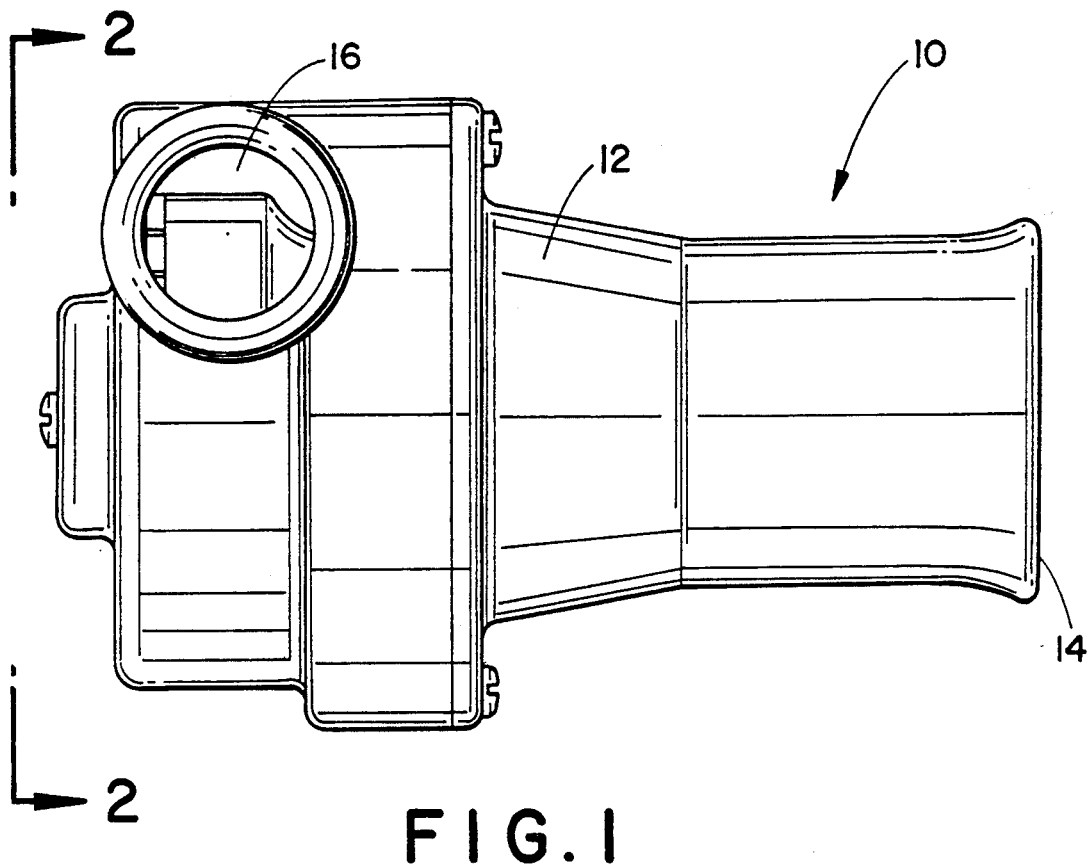
FIG. 1 is an elevated view of a pump formed in accordance with the present invention and particularly showing the pump housing and inlet and outlet passageways.

Referring now to the drawings wherein the showings are for purposes of illustrating the preferred embodiments of the invention only and not for purposes of limiting same, the FIGURES show a pump 10 comprised of a housing 12 and having an inlet 14 and an outlet 16. The pump can be sized for implantation within a living body and is preferably employed for pumping blood as a ventricle assist device for humans. It is to be noted that the pump can be sized so as to even be implantable within a heart chamber and thereby avoids the substantial problems incurred with heart pumps of larger sizes.

Figure 2:
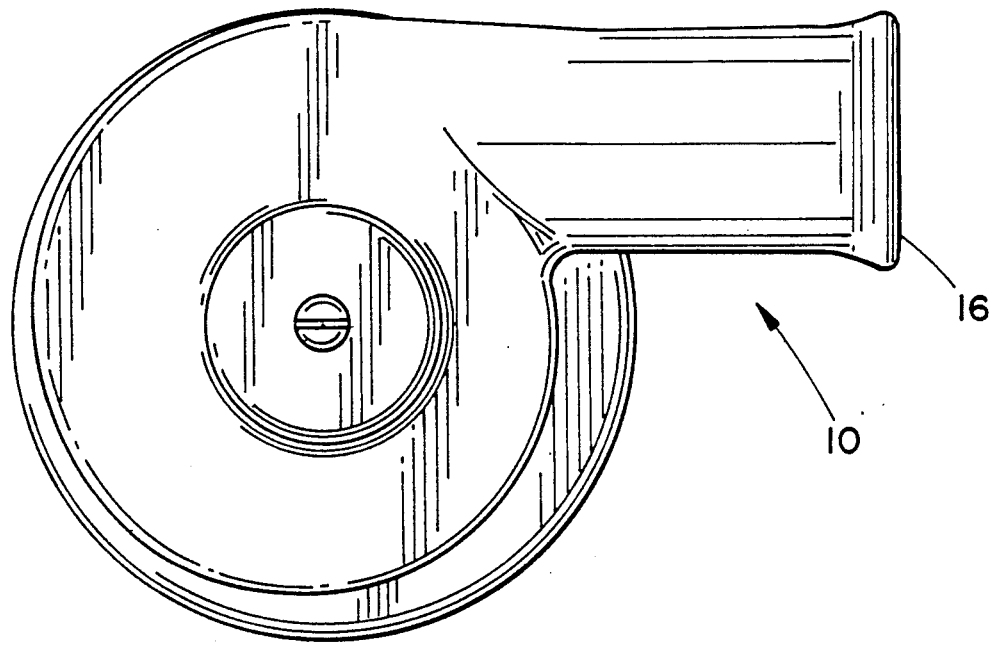
FIG. 2 is an elevated end view taken along lines 2—2 of FIG. 1.
Figure 3:
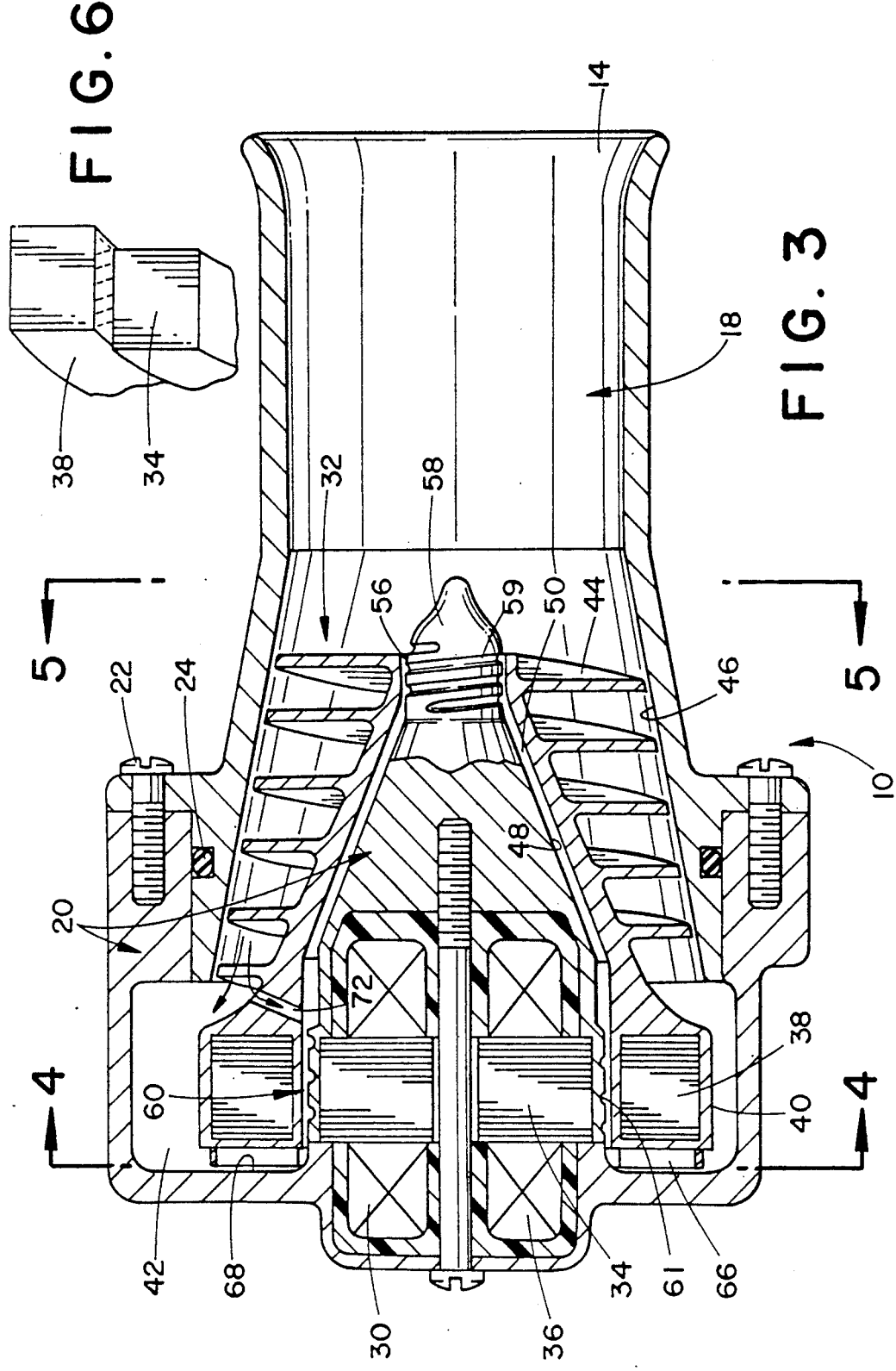
FIG. 3 is an enlarged cross-sectional view.

The pump 10 is a centrifugally operating pump so that the inlet 14 extends axially and the outlet 16 extends tangentially from the housing. With particular reference to FIGS. 1, 2, and 3, the housing 10 is shown to be more particularly comprised of an inlet portion 18 and a motor housing and outlet portion 20. The housing portions 18, 20 are constructed of a material suitable for living body implantation, and may be fastened together with conventional fastening devices 22, and sealed with a conventional sealing device such as an O-ring 24 at a location of overlapping engagement between the housing portions.

The housing 10 contains a motor 30, which can be either an AC or DC motor, and a rotatable pump rotor 31 having an impeller 32 which is magnetically driven by the motor for selective rotation relative to the housing. In the preferred embodiment of the invention, the motor 30 comprises an inverted or "inside out" motor in which the stator 34 and coils 36 are disposed radially inwardly of the motor rotor 38 disposed in an impeller base portion 40. Such an arrangement allows magnetic driving of the impeller by the rotor without a drive shaft. The permanent magnet rotor is received in the impeller and a ferrous material is received in the housing portion. Further, a seal which would seal the fluid passageway from the motor is obviated.

More particularly, first fluid passageway extends from the inlet 14 about the impeller, into an annular chamber 42 peripherally disposed about the impeller base portion 40 and ultimately to the outlet 16. As can be seen with reference to FIG. 3, the fluid flow passageway comprises a continuous passage containing a single moving part, the impeller 32, and avoids any seals or motor shafts such as is common in most prior pumps of this type.

Figure 4:
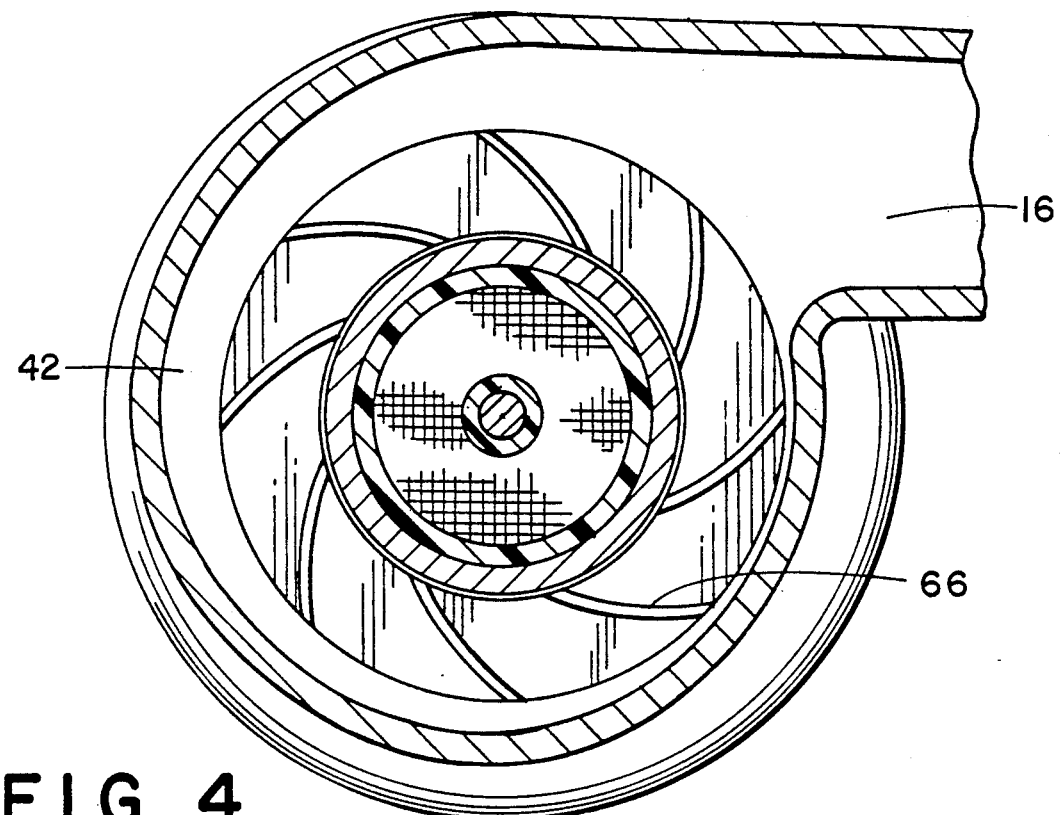
FIG. 4 is a cross-sectional view taken along lines 4—4 of FIG. 3.
Figure 5:
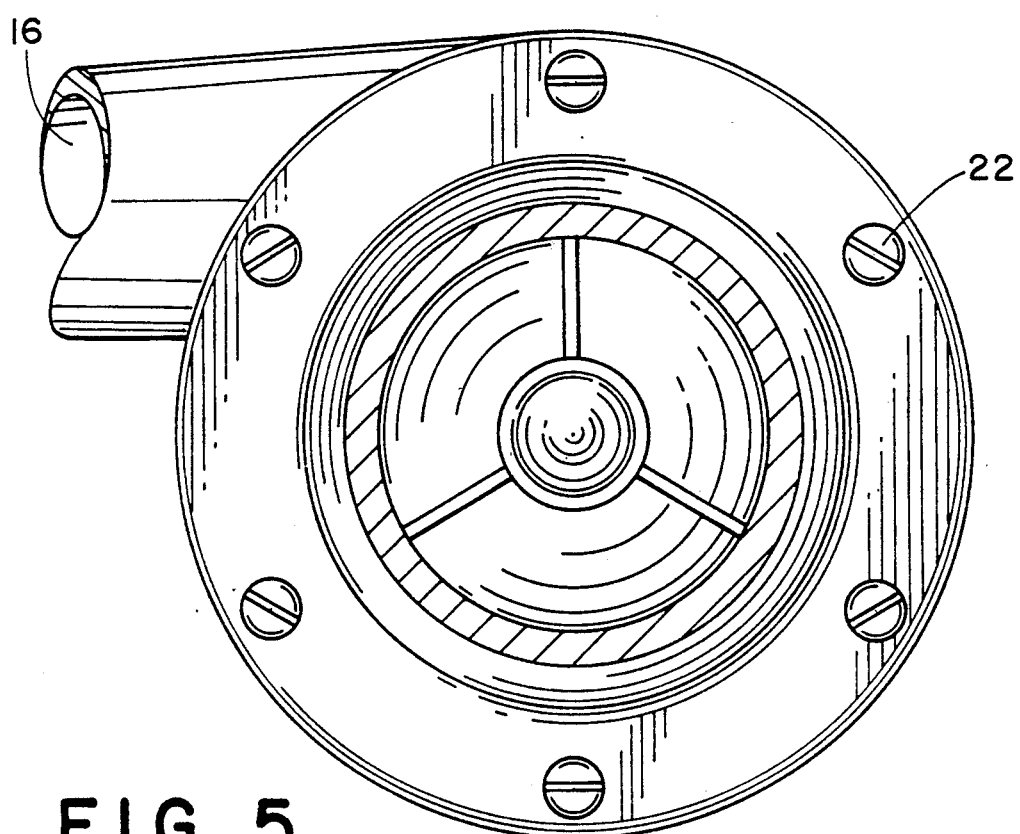
FIG. 5 is a cross-sectional view taken along lines 5—5 of FIG. 3.

With particular reference to FIGS. 3 and 4, since the pump is a centrifugally operating pump, the impeller includes a plurality of mixed flow impeller blades 44. The impeller shown is a three-bladed variable-lead screw. Since such a screw configuration may taper toward the inlet as shown, both the inlet portion 18 of the housing and the motor housing and outlet portion 20 opposite of the mixed flow impeller 44 matingly taper for close spacing between the inlet wall 46 and the motor housing wall 48. The spacing of the impeller relative to the housing wall 48 provides a second continuous passage 50 for bearing lubrication flow from the annular chamber 42 to the inlet. This passage is a relatively wide open, low velocity lube duct. The second fluid passageway 50 is defined by the annular passageway about the motor housing 20, intermediate the stator 34 and rotor 38, and is supplied by fluid from the volute chamber 42 with the fluid being urged through the passageway towards the inlet 14. The passage 50 narrows at opposed ends of the impeller 32 to define first and second fluid bearings during operation of the pump. The first bearing 56 is located at the terminal end portion of the motor housing portion 20 facing the inlet 14. The terminal portion 58 has a generally cone-like configuration and includes one or more extended helical grooves 59 to increase the lubricating and cooling flow through the fluid bearing 56. The second bearing similarly has a helically configured grooving 61 on the outer wall 48 of the stationary motor housing portion 20 to increase the bearing wash flow.

For improved blood pumping that avoids blood damage, the bearings must be well-washed by the continuous flow of blood through the passage 50. The second set of impeller blades 66 scavenges the blood from the passageway 50 intermediate the motor housing portion end wall 68 and the impeller 32 to control the flow and enhance the washing through the passageway 50 and about the impeller.

To further avoid stagnant blood locations and promote continuous fluid flow for good blood washing, the impeller includes openings 72 to permit fluid flow from the main impeller blades 44 and annular chamber 42 into the passageway 50.

With particular reference to FIG. 4, it may be seen that the annular chamber 42 is spirally offset relative to the generally circular dimension of the scavenge impeller 66. Such a configuration is generally conventional for the volute of a centrifugal pump, but the blood pump may be designed with a truly concentric discharge collector in place of the volute shown.

Because the impeller 32 is freely received in the housing 12 it is important that its rotational movement is controlled to avoid damage to the fluid passing through the pump. The fluid bearings 58, 60 control the radial spacing of the impeller from the stationary housing portion 20. However, the impeller will have a tendency to move away from the housing end wall 68 during operation. The magnetic attraction forces between the stator 34 and rotor 38 are designed to be sufficient to overcome this tendency, even with slight variation of movement, so that the rotationary movement of the impeller is effective. FIG. 6 illustrates that even when the stator and rotor are slightly offset, the invention is successfully operable.

When the pump is implanted in a human body, power to the pump is supplied by such conventionally known devices as an external battery or transformer apparatus.

The invention has been described with reference to the preferred embodiment. Obviously, modification and alterations will occur to others upon the reading and understanding of the specification. It is our intention to include all such modifications and alterations insofar as they come within the scope of the appended claims or the equivalents thereof.

Having thus described the invention, we now claim:

1. A blood pump for pumping blood through a living body, the blood pump comprising:
   a housing having an inlet and outlet in fluid communication with a chamber defined therein, the housing including a portion that extends axially inwardly into the chamber;
   an annular pump rotor received in the chamber around the housing portion for selective rotation relative to the housing for pumping blood from the inlet to the outlet, the pump rotor being spaced from the housing and housing portion to define radially spaced first and second passages, respectively;
   means for rotating the pump rotor relative to the housing;
   means for urging blood flow through the first passage;
   the second passage being narrowed at first and second ends for defining circumferentially continuous fluid bearings that support the pump rotor during pumping operation;
   first and second helical grooves axially spaced on the housing portion at the narrowed first and second ends of the second passage to increase blood flow through the fluid bearings;
   means for urging blood flow through the second passage in a direction independent from blood flow through the first passage; and
   an opening through the pump rotor for connecting the first and second passages to permit blood flow therebetween.

2. The blood pump as defined in claim 1 wherein the impeller pump rotor includes first and second sets of blades, the first blade set disposed in the first passage for pumping blood from the inlet toward the outlet.

3. The blood pump as defined in claim 2 wherein the second blade set is disposed on a rear face of the pump rotor and defines the urging means that scavenges blood from the chamber and enhances blood flow through the second passage.

* * * * *